United States Patent [19]

Gianakakos et al.

[11] 4,214,578
[45] Jul. 29, 1980

[54] ORTHOPEDIC BANDAGE HAVING IMPROVED CONFORMABILITY

[75] Inventors: Spiros Gianakakos, Highland Park; Franklin Boardman, Englishtown, both of N.J.

[73] Assignee: Johnson & Johnson, New Brunswick, N.J.

[21] Appl. No.: 852,766

[22] Filed: Nov. 18, 1977

[51] Int. Cl.$^2$ .............................................. A61L 15/07
[52] U.S. Cl. ...................................... 128/90; 528/495
[58] Field of Search ............... 128/90, 91, 91 R, 91 Q, 128/91 A; 528/495, 496

[56] References Cited

U.S. PATENT DOCUMENTS

| | | | |
|---|---|---|---|
| 2,842,120 | 7/1958 | Foglia et al. | 128/91 R |
| 2,842,138 | 7/1958 | Billings et al. | 128/91 R |
| 3,316,901 | 5/1967 | Smith | 128/91 R |
| 3,630,194 | 12/1971 | Boardman | 128/90 |
| 3,669,708 | 6/1972 | Reber et al. | 128/90 |
| 3,955,566 | 5/1976 | Stoffey | 128/90 |
| 4,052,282 | 10/1977 | Kubushiro | 128/90 |
| 4,102,338 | 7/1978 | Parker | 128/90 |

*Primary Examiner*—Robert W. Michell
*Assistant Examiner*—C. F. Rosenbaum

[57] ABSTRACT

The instant invention relates to an orthopedic bandage which hardens by means of a free radical catalyzed polymerization reaction, including 1,2-ditertiary glycol to improve the conformability thereof. The bandage comprises a flexible carrier having a cast forming composition comprising a monomer (polymerizable by means of a redox catalyst system) supported thereon, which monomer may be a solid, water-soluble, vinyl monomer such as diacetone acrylamide (DAA), N-isopropylacrylamide (N-IPA) or mixtures thereof. The preferred 1,2-ditertiary glycol is pinacol.

The polymerization of the above monomer is initiated by contacting the cast forming composition with water, in the presence of a redox catalyst system, e.g. by dipping the bandage, including the redox catalyst system supported thereon, in tap water.

The dipped bandage of the instant invention is soft, conformable and easy to wrap; unlike similar bandages which do not include the 1,2-ditertiary glycol.

8 Claims, No Drawings

ORTHOPEDIC BANDAGE HAVING IMPROVED CONFORMABILITY

FIELD OF INVENTION

The instant invention relates to an orthopedic bandage which hardens by means of a free radical catalyzed polymerization reaction, including a 1,2-ditertiary glycol to improve the conformability thereof. The bandage comprises a flexible carrier having a cast forming composition comprising a monomer (polymerizable by means of a redox catalyst system) supported thereon which monomer may be a solid, water-soluble vinyl monomer such as diacetone acrylamide (DAA), N-isopropylacrylamide (N-IPA) or mixture thereof. The preferred 1,2-ditertiary glycol is pinacol.

The polymerization of the above monomer is initiated by contacting the cast forming composition with water, in the presence of a redox catalyst system, e.g. by dipping the bandage, including the redox catalyst system supported thereon, in tap water.

BACKGROUND OF THE PRIOR ART

Plaster of paris supported on fabric or gauze has been used almost exclusively in the preparation of surgical casts designed to immobilize and support portions of the body, e.g. a leg arm, wrist, neck and the like. Plaster of paris is inexpensive, convenient and ready to use after simply dipping in water. Moreover, practically all physicians, particularly orthopedic specialists, have long worked with the plaster of paris medium and are very familiar with the application. Once having mastered the art of working with plaster of paris they are reluctant to learn the different techniques associated with other media.

Nonetheless plaster of paris has certain shortcomings. It is relatively heavy and can be damaged by wetting with water. It is also substantially opaque to x-rays, thus sometimes requiring that a cast be removed to ascertain, for example, whether a fracture has healed satisfactorily.

The various aforementioned problems with plaster of Paris orthopedic bandages have led to the development of orthopedic bandages such as the bandage described in U.S. Pat. No. 3,630,194. This bandage utilizes as a cast forming composition a mixture including a water soluble monomer selected from the group consisting of DAA, N-IPA and mixtures thereof, said monomers being polymerizable, in the presence of water, by means of a redox catalyst system which comprises an oxidation component and a reducing agent. This bandage is hardened in a manner similar to the prior art plaster of paris bandages by dipping the bandage into tap water. The advantage of this method of initiation is that, unlike certain other bandages which use thermoplastic sheets or apply hardenable resins from a paste, the technician working with the bandage does not have to learn new techniques for preparing a cast.

Although satisfactory in many ways, it has been found that the orthopedic bandages described in U.S. Pat. No. 3,630,194 suffered from certain drawbacks. For example, the bandages, after dipping in water to initiate the hardening thereof, are stiff, non-conformable to the limb and difficult to wrap. As further discussed below, it has been found that the addition of a 1,2-ditertiary glycol to the cast forming composition alleviates the above drawbacks. Furthermore, pinacol, the preferred 1,2-ditertiary glycol from the standpoint of improved conformability, also unexpectedly increases the working time of the instant orthopedic bandage.

SUMMARY OF THE INVENTION

The instant invention relates to a novel orthopedic bandage, comprising a cast forming composition supported on a flexible carrier, said cast forming composition comprising a redox catalyst system, a water soluble, solid, vinyl monomer polymerizable by means of said redox catalyst system, and a 1,2-ditertiary glycol. The water soluble, solid, vinyl monomer is preferably selected from DAA, N-IPA and mixtures thereof.

The orthopedic bandage so formulated is prepared for use by contacting it with an aqueous medium, preferably hot tap water, in the presence of a catalytic amount of a redox catalyst, e.g. a copper salt, whereby the vinyl monomer is polymerized. The polymerization catalyst may be added to the aqueous medium itself, or it may be incorporated into the cast forming composition. In the latter case, the bandage must be kept dry and out of contact with moisture laden air. Because both the copper salt and the reducing agent are required to initiate the polymerization reaction, one catalytic component may be excluded from the cast-forming composition and added to the water at the time the bandage is dipped, thus minimizing the sensitivity of the bandage to water or moisture laden air.

Both components of the catalyst may be incorporated in the cast forming composition so that orthopedists need only dip the bandage in water in order to initiate polymerization and prepare the bandage for use. This simple procedure substantially duplicates, of course, the conventional techniques employed in preparing plaster of paris casts. If the entire catalyst is not incorporated in the cast forming composition, the orthopedist will need to add any missing catalytic component to the water in which the bandage is immersed.

It has been found, as before noted, that without the 1,2-ditertiary glycol the bandage is stiff, non conformable and difficult to wrap around the limb to be immobilized. However the incorporation of 1,2-ditertiary glycol at a level of from 0.2 to 10%, preferably 0.5 to 2%, of the total weight of the coated bandage improves the conformability of the bandage.

The preferred flexible carrier for formulating the instant novel bandages is fiberglass. This fabric is preferred since it adds to the strength of the cast, especially during the earlier stages following activation. That is, fiberglass contributes to the 'green strength' of casts formed from the bandage. Fiberglass fabrics which are fashioned from a very brittle fiber are especially notable for their non conformability. The incorporation of a 1,2-ditertiary glycol in a bandage utilizing a fiberglass fabric provides conformability and ease of wrapping without detracting from the desirable strength properties of fiberglass based bandages. Suitable 1,2-ditertiary glycols which may be used are described by the general formula:

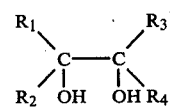

where $R_1$, $R_2$, $R_3$ and $R_4$ are alkyl groups, e.g. $C_1$ to $C_5$ alkyl groups.

The most preferred 1,2-ditertiary glycol is pinacol (where $R_1=R_2=R_3=R_4=CH_3$). Pinacol also, as further demonstrated below, provides increased working time whereby the technician fabricating a cast has more time prior to the bandage hardening to a point where it is difficult to wrap. Pinacol, however, does not interfere with overall set time nor does it detract from the 'green strength'.

Reducing agents that are useful in preparing redox catalyst systems are known in the art and include ferrous sulfate, sodium sulfite, sodium dithionate, ferrous chloride, sodium formaldehydesulfoxylate, oxalic acid, cobalt (II) chloride and hydrazine. All of the reducing agents known in the art as suitable components for redox catalyst systems may be used in the practice of the instant invention.

A copper salt may function as the oxidizing agent of the redox catalyst system. The copper salt is generally characterized as being partially soluble in water at room temperature. Very soluble copper salts (e.g. the sulfate and chloride) release such massive concentrations of copper ions in water that polymerization of the monomer is rapid and the setting time of a bandage is difficult to control. Partially soluble copper compounds (e.g. the acetylacetonate) release just enough copper ion to produce a bandage with a practical working time (60–70 seconds). Very insoluble copper compounds (e.g. the phosphate) do not release enough copper ion to efficiently initiate polymerization.

The oxidizing agent, e.g. a copper salt, may comprise from 0.0005" to 5%, preferably from 0.0005" to 1.0%, and most preferably from 0.01 to 0.10% by weight of the bandage (either incorporated in the bandage or in the dip water). The molar ratio of reducing agent to copper salt may vary from 1 to 9 to 9 to 1, preferably about 1 to 1.

The cast forming composition may comprise from 50 to 80%, preferably 200 to 500%, by weight based on the weight of the flexible carrier. Of the total solids in the cast forming composition the monomer may comprise from about 30 to 100%, preferably 50 to 80%, by weight of the total. The remainder will include binders, fillers, comonomers (other than the water soluble, solid, vinyl monomers), the redox catalyst components (if incorporated in the cast forming composition) etc.

The instant novel bandages may be prepared, packaged and used in a manner similar to the bandage described in U.S. Pat. No. 3,630,194. Materials suitable for preparing said novel bandage including the redox catalyst, the flexible carrier, the monomer, comonomers, binders, fillers, polymerization rate controllers, etc. are also disclosed in said patent and the disclosure of said patent is hereby incorporated herein by reference to describe such materials as well as the methods of preparation, packaging and use of the instant novel bandages. No buffers are necessary if a copper salt is utilized in the orthopedic bandage of the instant invention. When persulfates are used as initiators, however, large amounts of persulfates are required, which, since persulfates decompose to acidic by-products which are harmful to skin, require a buffer. Because so little copper may be used as the oxidizing agent, the pH of the wet bandage does not change. Sodium sulfite, the preferred co-reactant with cupric acetylacetonate, acts as its own buffer.

The following examples illustrate the above described invention. However, there is no intent to limit the claims thereto.

EXAMPLE 1

Example of Preparation of a Pinacol Containing Bandage

A fiberglass fabric is passed at a rate of 8 ft/min. through a melt containing 975 parts of diacetone acrylamide, 20 parts of a polyethylene oxide such as Carbowax 4000, available from Union Carbide Corp., New York, N.Y., 43 parts of pinacol and 10 parts of a molecular sieve such as molecular sieves 3A, available from Union Carbide Corp., Linde Division, New York, N.Y. A catalyst mixture containing 136 parts of a pre-blend (pre-blend contains 960 parts of sodium sulfite and 40 parts of cupric acetylactonate) 644 parts of sodium sulfite, and 17 parts of a high molecular weight (about 5,000,000 M.W.) polyethylene oxide such as Polyox Coagulant Grade, available from Union Carbide Corp., Chemicals and Plastics Div., New York, N.Y., is sprinkled on at a rate of 6 gm/min. before the melt solidifies. The impregnated fabric is then cut into 3 yard-long bandages.

EXAMPLE 2

Preparation of a Bandage with No Softener

A fiberglass fabric was passed at a rate of 30 ft/min. through a melt consisting of 975 parts of diacetone acrylamide, 20 parts of Carbowax 4000, 30 parts of Aerosil R-972, (a fumed silica) and 10 parts of Molecular Sieves (type 3A).

A blend of 106 parts of a mixture of sodium sulfite (24 parts) and cupric acetylacetonate (1 part), 694 parts of sodium sulfite, and 22 parts of Polyox was sprinkled at a rate of 11 gm/min. on the fabric emerging from the melt.

When the melt was completely frozen on the fabric, the fabric was ready for use.

EXAMPLE 3

Preparation of a Bandage Containing Trimethylolpropane

A fiberglass fabric was passed at a rate of 30 ft/min. through a melt containing 975 parts of diacetone acrylamide, 20 parts of Carbowax 4000, 30 parts of Aerosil R-972, 43 parts of trimethylolpropane and 10 parts of Molecular Sieves, (type 3A).

The fabric emerging from the melt was sprinkled at the rate of 11 gm/min. with a blend of 694 parts of sodium sulfite, 22 parts of Polyox (coagulant Grade), and 106 parts of a mixture of sodium sulfite (24 parts) and cupric acetylacetonate (1 part).

When the melt on the fabric was completely frozen, the fabric was ready for use.

It was found that Aerosil R-972, when added to the bandage formulation, prevents melting of the solids on a bandage stored at 120° F. Melting at 120° F. occurs only when a softener (pinacol, trimethylolpropane, etc.) is in the formulation.

EXAMPLE 4

Testing of Bandages for Conformability

The above bandages were placed in an Instron Testing Machine to measure the ease of deflection of the bandage. The bandage was horizontally stretched over two posts, one inch apart. Midway between the two posts was a third post that came down at the rate of one inch per minute toward the top surface of the bandage.

The force required to deflect the bandage one-half inch was compared for the three bandages:

TABLE

Comparison of Softener and the Force Required to Deflect a Softened Bandage

| Preparation Described in Example No. | Softener | Deflection Force (kg) |
| --- | --- | --- |
| 1 | Pinacol | 12.2 |
| 2 | None | 43.0 |
| 3 | Trimethylolpropane* | 17.2 |

*Trimethylolpropane was chosen as an examle of a polyol which is not a ditertiary glycol.

The lower the deflection force, the more conformable the bandage will be upon wrapping. The bandage containing pinacol required only 12.2 kg for deflection, while a bandage with no softener required 43 kg. A bandage made with the best alternative softener that could be found (trimethylolpropane) required 17 kg of force. The difference of 4.8 kg between pinacol and trimethylolpropane softened bandages is significant, since a wrapper will feel that the pinacol bandage is more limp.

What is claimed:

1. An orthopedic bandage having improved conformability which comprises a cast forming composition supported on a flexible carrier, said cast forming composition including a water-soluble solid, vinyl monomer, a catalyst capable of polymerizing said monomer in the presence of water, and a 1,2 ditertiary glycol.

2. The orthopedic bandage of claim 1 wherein said monomer is selected from the group consisting of diacetone, acrylamide, N-isopropyl acrylamide, and mixtures thereof.

3. The orthopedic bandage of claim 1 wherein said catalyst is a redox catalyst system.

4. The orthopedic bandage of claim 1 wherein said redox catalyst comprises a copper salt oxidant.

5. The orthopedic bandage of claim 1 wherein said 1,2 ditertiary glycol is pinacol.

6. The orthopedic bandages of claim 5 wherein said pinacol comprises from 0.5 to 2% of the total weight of the coated bandage.

7. The orthopedic bandage of claim 1 wherein said flexible support is a woven fiberglass.

8. The orthopedic bandage of claim 1 wherein said 1,2-ditertiary glycol comprises from 0.2 to 10% of the total weight of the coated bandage.

* * * * *